United States Patent [19]
Castrogiovanni et al.

[11] Patent Number: 5,302,380
[45] Date of Patent: Apr. 12, 1994

[54] COSMETIC COMPOSITIONS CONTAINING ATACTIC POLYPROPYLENES AND RELATED METHODS

[75] Inventors: Anthony Castrogiovanni, Belford; Joseph F. Calello, Union, both of N.J.; Arvind Shah, Owings Mills, Md.; Steven Amato, Clifton, N.J.

[73] Assignee: Revlon Consumer Products Corporation, New York, N.Y.

[21] Appl. No.: 895,065

[22] Filed: Jun. 8, 1992

[51] Int. Cl.$^5$ .................. A61K 7/021; A61K 7/025
[52] U.S. Cl. .............................. 424/63; 424/64; 424/401
[58] Field of Search .............. 424/401, 63, 64, 69, 424/28.31

[56] References Cited

U.S. PATENT DOCUMENTS

| | | | |
|---|---|---|---|
| 3,574,827 | 4/1971 | Beerbower | 424/401 X |
| 4,847,340 | 7/1989 | Allen | 424/401 X |
| 4,859,757 | 8/1989 | Pellon | 424/401 X |
| 5,093,110 | 3/1992 | Kamen et al. | 424/401 |
| 5,118,432 | 6/1992 | Emert et al. | 252/49.6 |

OTHER PUBLICATIONS

Eastman Amorphous Polyolefins, 1990.

Primary Examiner—Thurman K. Page
Assistant Examiner—Peter F. Kulkosky
Attorney, Agent, or Firm—Julie Blackburn

[57] ABSTRACT

A cosmetic composition comprising 0.1–20% of an atactic polypropylene having 50–100% atactic content, 0.1–15% crystallinity, and a molecular weight of 1,000–10,000.

8 Claims, No Drawings

COSMETIC COMPOSITIONS CONTAINING ATACTIC POLYPROPYLENES AND RELATED METHODS

TECHNICAL FIELD

The invention is in the field of cosmetic compositions containing atactic polypropylene.

BACKGROUND OF THE INVENTION

Atactic polypropylenes are polyalphaolefin resins. Certain varieties of these resins are used in caulks, sealants, hot melt adhesives, and in rubber compounding.

U.S. Pat. No. 3,574,827 to Beerbower discloses lotions and ointments containing highly crystalline polypropylenes exhibiting 80-95 isotactic content. Beerbower teaches that isotactic polypropylenes are essential to providing creams and lotions which adhere well to skin, and that polypropylene polymers containing greater than 20% atacticity result in stringy, tacky, cosmetically unacceptable creams or ointments.

It has been unexpectedly discovered that the incorporation of atactic polypropylenes of low crystallinity and isotactic content into cosmetic compositions enhances wear and adherence of the cosmetic composition to skin as well as providing smooth, rich, cosmetically acceptable compositions.

SUMMARY OF THE INVENTION

The invention is directed to a cosmetic composition comprising about 0.1-20% of an atactic polypropylene having about 50-100% atactic content, 0.1-15% crystallinity, and a molecular weight of about 1,000-10,000.

The invention is also directed to method for improving adhesion of cosmetic compositions to skin comprising adding to said composition 0.1-20% of an atactic polypropylene having 50-100% atactic content, 0.1-15% crystallinity, and a molecular weight of 1,000-10,000.

DETAILED DESCRIPTION

The term "molecular weight" means average number molecular weight.

The term "atactic content" means that the polypropylene polymeric structure is random or without orientation, as opposed to isotactic or syndiotactic polymers which exhibit specific orientation and structural regularity. Isotactic and syndiotactic polymers, due to their structural regularity, can easily cross link to form a crystalline network whereas the structural irregularity of atactic polymers precludes appreciable polymeric cross linking:

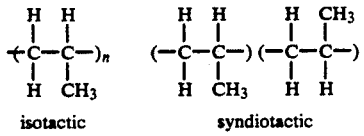

The term "crystallinity" refers to the degree of cross linking of the polypropylene polymer. Crystallinity is directly proportional to the degree of polymeric cross linking, and polymers which exhibit extensive cross linking are highly crystalline in nature.

All percentages set forth refer to percentages by weight of the total composition.

The term "cosmetic composition" means cosmetic compositions applied to hair or skin. The preferred cosmetic compositions are make up, eyeshadow, blush, sunscreen, and lipstick.

"Improved adherence" or "adhesion" means that the ingredients found in the cosmetic compositions, such as pigments, powders, sunscreen chemicals, oils, or waxes, etc. adhere more readily to the skin thus resulting in a longer wearing cosmetic composition.

Incorporation of 0.1-20%, preferably 0.5-5.0% of the specific atactic polypropylenes mentioned herein, into cosmetic compositions will provide compositions which adhere well to the skin, are longer lasting, and do not exhibit stringiness, tackiness, or granularity found in the prior art compositions. In fact, cosmetic compositions containing the atactic polypropylenes of the invention are very smooth, apply well, and are very cosmetically acceptable. The preferred cosmetic compositions of the invention include sunscreen, lipstick, eyeshadow, blush, and makeup.

Preferably, the atactic polypropylenes used in the cosmetic compositions of the invention have a softening point of 15°-160° C. when measured by the ATSM E28 method well known to those skilled in the art.

A suitable eyeshadow in accordance with the invention comprises about 0.1-50% pigment, 1.1-40% wax, and 0.1-60% oil, and in addition may contain a variety of other ingredients such as preservatives, powders, and so forth. A suitable lipstick comprises, in addition to 0.1-20% atactic polpropylene, about 0.1-50% pigment, 0.1-80% wax, and 0.1-50% oil. A suitable blush comprises about 0.1-60% pigment, 0.1-50% wax, and about 0.1-60% oil. A suitable makeup comprises about 0.1-40% pigment, 0.1-60% water, and 0.1-60% oil.

Suitable pigments are the FD&C and D&C colors, as well as other organic and inorganic pigments generally used in cosmetic compositions such as iron oxides, titanium dioxide, boron nitride, mica, bismuth oxychloride, talc, titanated mica, carmine, and so on.

Suitable oils include various silicone oils such as cyclomethicone, dimethicone, cetyl dimethicone copolyol, etc; in addition to oils such as octyl palmitate, tridecyl neopentanoate, polyisobutene, polyglyceryl 3-diisostearate, isostearyl neopentanoate, isooctyl hexanoate, castor oil, and so on.

Suitable waxes include beeswax, carnauba, ceresin, microcrystalline, lanolin, trilaurin, octacosanol, paraffin, ozokerite, candelilla, shellac, stearyl wax, capok wax, bayberry, etc.

The cosmetic compositions of the invention may also contain preservatives, powders, humectants, emollients, moisturizers, film formers, and so on.

Most preferred is a cosmetic composition containing an atactic polypropylene selected from the group consisting of an atactic polypropylene having a softening point of 20° C. and a molecular weight of 2,000; an atactic polypropylene having a softening point of 135° C. and a molecular weight of 5,600; and an atactic polypropylene having a softening point of 150° C. and a molecular weight of about 4,400.

The invention is also directed to a method of improving adhesion of a cosmetic composition to skin or hair comprising adding to said composition 0.1-20% of an atactic polypropylene having 50-100% atactic content, 0.1-15% crystallinity, and a molecular weight of 1,000-10,000.

Preferably about 0.5–5.0% of the atactic polypropylene is added to the cosmetic composition. The cosmetic composition is made in the usual manner, please specify.

The invention will be described in connection with the following examples which are set forth for the purpose of illustration only.

EXAMPLE 1

An eyeshadow stick was made as follows:

|  | w/w % | | |
| --- | --- | --- | --- |
|  | blue | teal | blue |
| $C_9$-$C_{11}$ isoparaffin | 5.00 | 5.00 | 9.00 |
| Cyclomethicone | 16.80 | 16.80 | 15.00 |
| Cyclomethicone | 16.80 | 16.80 | 15.00 |
| Octyl palmitate | 6.00 | 6.00 | 5.00 |
| Polyisobutene | 0.625 | 0.625 | 0.500 |
| Polyglyceryl 3 isostearate | 1.20 | 1.20 | 1.20 |
| M/P/E/B paraben phenoxyethanol | 1.00 | 1.00 | 1.00 |
| silica silylate | 0.60 | 0.60 | 0.70 |
| Bentone 38 | 0.66 | 0.66 | 0.66 |
| Propylene carbonate | 0.22 | 0.22 | 0.22 |
| Titanium dioxide | 2.00 | 2.00 | 4.00 |
| Silica | 5.00 | 5.00 | 5.00 |
| Boron nitride | 0.50 | 0.50 | 1.00 |
| Silica/mineral oil/TiTO$_2$ | 0.40 | — | 0.60 |
| Iron oxide yellow | — | 0.10 | — |
| Iron oxide black | 0.50 | 0.50 | 0.40 |
| Ultramarine blue | 3.50 | 1.80 | 2.80 |
| Ultramarine violet | 0.80 | — | 0.70 |
| Iron oxide green | — | 7.00 | — |
| 50/50 9484 | — | 0.10 | — |
| Talc | 6.395 | 2.195 | 4.24 |
| Carmine | 0.40 | — | 0.08 |
| BiOCl | 4.00 | 4.00 | 4.00 |
| TiO$_2$/mica | — | — | 1.00 |
| Sericite | 5.00 | 5.00 | 4.00 |
| Carnauba | 0.30 | 0.30 | 0.30 |
| Ceresin | 3.00 | 3.00 | 3.00 |
| Octacosanol | 6.00 | 6.00 | 6.00 |
| Trilaurin | 2.50 | 2.50 | 2.50 |
| Synthetic wax | 2.20 | 2.20 | 2.20 |
| Lanolin alcohol | 0.30 | 0.30 | 0.30 |
| Beeswax | 0.60 | 0.60 | 0.60 |
| Atactic polypropylene | 1.00 | 1.00 | 1.00 |
| Ethylene vinyl acetate | 1.00 | 1.00 | 1.00 |
| Octyl palmitate | 6.00 | 6.00 | 6.00 |

EXAMPLE 2

A lipstick formulation was made as follows:

|  | w/w % |
| --- | --- |
| Candelilla wax | 7.50 |
| Carnauba wax | 2.20 |
| Ceresin | 2.50 |
| Paraffin | 1.00 |
| Cetyl acetate 90%/acetylated lanolin alcohol 10% | 12.00 |
| PVP hexadecene | 2.00 |
| Castor oil | 26.00 |
| Lanolin oil | 10.20 |
| Octyl palmitate | 5.50 |
| Glyceryl triacetyl ricinoleate | 9.50 |
| Quaternium 18 hectorite | 1.00 |
| Acrylates copolymer | 0.50 |
| Polypropylene Polypol 19 | 0.50 |
| silica | 0.20 |
| botanical salts | 1.00 |
| octyl methoxy cinnamate | 2.20 |
| mica/mimosa wax | 0.20 |
| oleyl alcohol | 4.00 |
| cetyl alcohol | 4.00 |
| fragrance | 0.50 |
| pigment/pearls/mica | 11.00 |
| Methyl paraben | 0.30 |
| Propyl paraben | 0.10 |

-continued

|  | w/w % |
| --- | --- |
| BHA | 0.10 |

The lipstick composition was made by melting the waxes and oils, adding the pigments and other ingredients. The lipstick was molded and cooled.

EXAMPLE 3

Revlon's Super Lustrous Lipstick (High Bean Copper) was compared with a Revlon Super Lustrous Lipstick formulation to which Polypol 19 (Crowley Chemical) and a Revlon Super Lustrous Lipstick formulation to which Eastobond M5FS (Eastman Chemical Company) were added as set forth below:

|  | Control | 1 | 2 | 3 |
| --- | --- | --- | --- | --- |
| Revlon Super Lustrous | | | | |
| Lipstick | 100.0 | 99.0 | 96.0 | 99.0 |
| Polypol 19 | — | 1.0 | 4.0 | — |
| Eastobond M5FS | — | — | — | 1.0 |

Both Polypol 19 and Eastobond M5FS provide a creamier lipstick formulation. When the lipstick formulations were placed on skin and blotted with tissue paper, the formulations containing Polypol 19 and Eastobond M5FS did not transfer as readily to tissue paper.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the appended claims.

We claim:

1. A cosmetic composition selected from the group consisting of an eyeshadow containing 0.1–50% pigment, 0.1–40% wax, and 0.1–60% oil, a lipstick containing 0.1–50% pigment, 0.1–80% wax, and 0.1–50% oil, a blush containing 0.1–60% pigment, 0.1–50% wax, and 0.1–60% oil, and a makeup containing 0.1–40% pigment, 0.1–60% water, and 0.1–60% oil comprising 0.5–5% of an atactic polypropylene consisting essentially of 50–100% atactic content, 0.1–15% crystallinity, and a molecular weight of 1,000–10,0000, said composition having improved adherence to skin as compared to the same composition not containing said atactic polypropylene.

2. The composition of claim 1 wherein the atactic polypropylene has a softening point of 15°–160° C.

3. The composition of claim 1 wherein the atactic polypropylene has a softening point of 20° C. and a molecular weight of 2,000.

4. The composition of claim 1 wherein the atactic polypropylene has a softening point of about 135° C. and a molecular weight of 5,600.

5. The composition of claim 1 wherein the atactic polypropylene has a softening point of 150° C. and a molecular weight of about 4,400.

6. A method of improving adhesion of a cosmetic composition selected from the group consisting of an eyeshadow containing 0.1–50% pigment, 0.1–40% wax, and 0.1–60% oil, a lipstick containing 0.1–50% pigment, 0.1–80% wax, and 0.1–50% oil, a blush containing 0.1–60% pigment, 0.1–50%wax, and 0.1–60% oil, and a makeup containing 0.1–40% pigment, 0.1–60% water, and 0.1–60% oil to skin comprising adding to said composition 0.5–5% of an atactic polypropylene consisting essentially of 50–100% atactic content, 0.1–15% crystallinity and a molecular weight of 100–10,000 wherein the adherence to skin of said composition is improved as compared to the same composition not containing said atactic polypropylene.

7. The method of claim 6 wherein the atactic polypropylene has a softening point of 15°–160° C.

8. The method of claim 7 wherein the cosmetic composition comprises 0.5–5% atactic polypropylene.

* * * * *